US00PP21409P2

(12) United States Plant Patent
Dusek et al.

(10) Patent No.: US PP21,409 P2
(45) Date of Patent: Oct. 19, 2010

(54) ***GAILLARDIA* PLANT NAMED 'EL FUEGO'**
(50) Latin Name: *Gaillardia×aristata*
Varietal Denomination: El Fuego

(76) Inventors: John Dusek, 7010 S. Graham Rd., St. Charles, MI (US) 48655; Jennifer Ohman-Dusek, 7010 S. Graham Rd., St. Charles, MI (US) 48655

( * ) Notice: Subject to any disclaimer, the term of this patent is extended or adjusted under 35 U.S.C. 154(b) by 0 days.

(21) Appl. No.: 12/378,900

(22) Filed: Feb. 20, 2009

Related U.S. Application Data

(60) Provisional application No. 61/067,761, filed on Feb. 28, 2008.

(51) Int. Cl.
*A01H 5/00* (2006.01)

(52) U.S. Cl. ..... Plt./431

(58) Field of Classification Search ..... Plt./431
See application file for complete search history.

*Primary Examiner*—June Hwu

(57) ABSTRACT

'EL FUEGO' is distinguishable by compact habit, gray-green foliage and fiery-red tubular ray flowers. In combination these traits set 'EL FUEGO' apart from all other existing varieties of *Gaillardia* known to the inventor.

2 Drawing Sheets

Genus: *Gaillardia.*

Species: ×*aristata.*

Denomination: 'EL FUEGO'.

BACKGROUND OF THE INVENTION

The present invention relates to a new and distinct cultivar of *Gaillardia*, commonly known as blanket flower, a hardy perennial for use in planted container, garden, and landscape. The new cultivar, from the family Asteraceae formerly named Compositae, is known botanically as *GAILLARDIA×aristata* and will be referred to hereinafter by the cultivar name 'EL FUEGO'.

'EL FUEGO' was discovered by the inventor in 2005, as a single non-induced whole plant sport or mutation which the inventor observed at flowering time in a growing crop of plants of *Gaillardia aristata* 'Burgundy' (unpatented). Discovery occurred at the inventor's garden in Freeland, Mich. Both 'Burgundy' and 'EL FUEGO' bear red flowers. However, the flowers of 'EL FUEGO' are comprised of tubular ray flowers, whereas the ray flowers of 'Burgundy' are flat. The closest comparison plant known to the inventor is the tubular-flowered *Gaillardia* variety named 'FANFARE' (U.S. Plant Pat. No. 15,892). 'EL FUEGO' is readily distinguishable from the comparison plant by flower color since the flowers of 'FANFARE' are bi-colored yellow and red.

'EL FUEGO' exhibits compact habit, elongated gray-green leaves, and fiery-red flowers. The large daisy-like inflorescence is composed of tubular-shaped ray flowers. Plants of 'EL FUEGO' bloom from the middle of summer through late summer. In flower 'EL FUEGO' ranges from 35-40 cm. in height and reaches 25 cm. in width in a 1-liter container. Cultural requirements include full sun, moist well-draining soil, and moderate water. Hardiness is classified as USDA Zone 5.

First asexual propagation of 'EL FUEGO' was conducted by the inventor in 2006, at the inventor's nursery in St. Charles, Michigan. The method of propagation used for asexual propagation was vegetative cuttings. Since that time, under close observation the distinguishing characteristics of 'EL FUEGO' have remained fixed, stable, and have been found to reproduce true to type in successive generations of asexual propagation.

SUMMARY OF THE INVENTION

The following traits represent the distinguishing characteristics of 'EL FUEGO'.

These traits in combination distinguish 'EL FUEGO' from all other existing varieties of *GAILLARDIA* known to the inventor. 'EL FUEGO' has not been tested under all possible conditions and phenotypic differences may be observed with variations in environmental, climatic, and cultural conditions, however, without any variance in genotype.

1. 'EL FUEGO' is an herbaceous flowering perennial.
2. 'EL FUEGO' exhibits large daisy-like inflorescences composed of tubular-shaped ray flowers.
3. The ray flowers in each inflorescence of 'EL FUEGO' are fiery-red in color.
4. 'EL FUEGO' exhibits elongated gray-green leaves.
5. 'EL FUEGO' ranges from 35-40 cm. in height and reaches 25 cm. in width when grown to flowering in a 1-liter container.
6. 'EL FUEGO' is hardy to USDA Zone 5.
7. 'EL FUEGO' grows well in full sun and moist well-draining soil, with moderate water.
8. 'EL FUEGO' blooms from the middle of summer through late summer.

BRIEF DESCRIPTION OF THE DRAWINGS

The accompanying color drawings illustrate the overall appearance of 'EL FUEGO' showing color as true as is reasonably possible to obtain in color reproductions of this type. Color in the drawings may differ from color values cited in the detailed botanical description, which accurately describe the actual color of 'EL FUEGO'.

The drawing labeled

The drawing labeled

Figure 1:
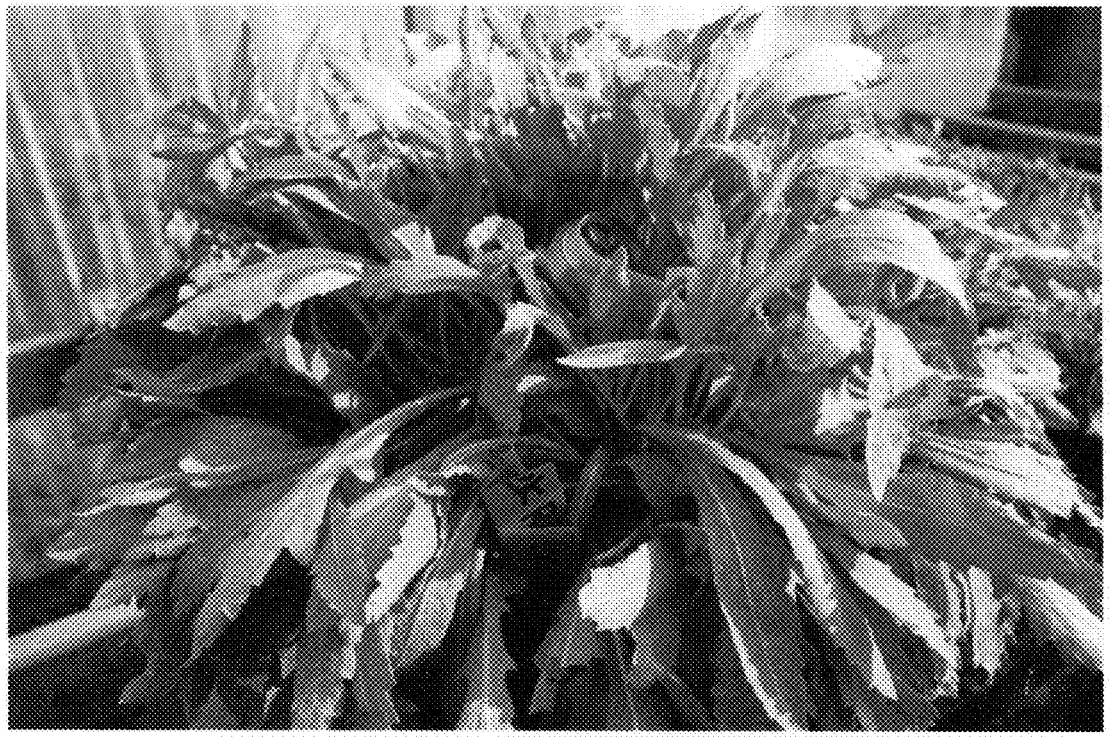
FIG. 1 depicts a whole plant of 'EL FUEGO', which is 18 months-old and has been grown out of doors in Watsonville, Calif. and then in Arroyo Grande, Calif. where the drawing was made and the botanical data collected.
Figure 2:
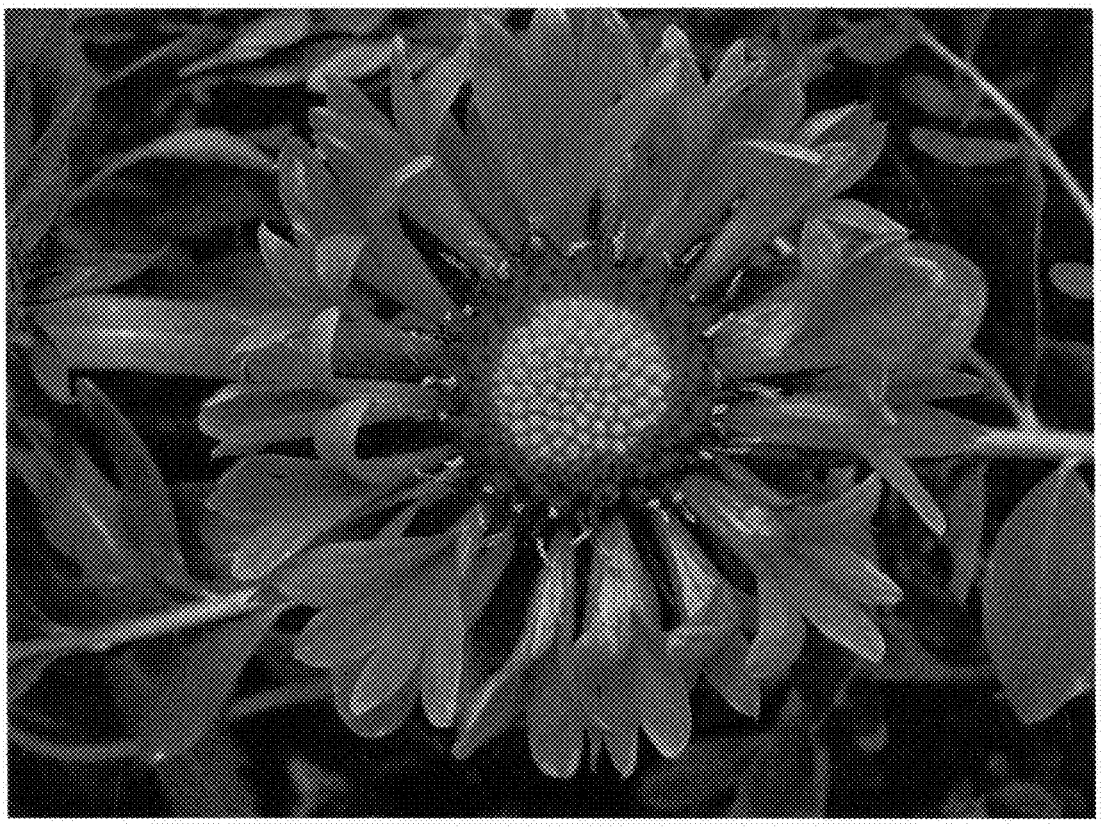
FIG. 2 depicts a close-up view of a single inflorescence of 'EL FUEGO'.

Both drawings were made using conventional techniques and although flower and foliage may appear different from actual color due to light reflectance, their color is as accurate as possible by conventional photography.

BOTANICAL DESCRIPTION OF THE PLANT

The following is a detailed botanical description of 'EL FUEGO'. Unless otherwise stated herein, observations, measurements, values and comparisons were compiled from 18 months-old plants grown out of doors in Watsonville, Calif. and then in Arroyo Grande, Calif. where the botanical data was collected. Color determinations are made in accordance with The 2001 Royal Horticultural Society Colour Chart from London, England, except where general color terms of ordinary dictionary significance are used. Growing conditions are similar to the species.

Botanical classification: *GAILLARDIA×aristata* 'EL FUEGO'.
Family: Asteraceae (formerly Compositae).
Genus: *GAILLARDIA.*
Species: *×aristata.*
Denomination: 'EL FUEGO'.
Common name: Blanket flower.
Parentage: *GAILLARDIA×aristata* 'EL FUEGO' was discovered as a sport derived from the following parent:
Parent: An individual *Gaillardia aristata* 'Burgundy' (unpatented).
Propagation method: Vegetative cuttings.
Rooting system: Fine and fibrous.
Vigor: Vigorous.
Time to develop roots (range): 14 to 20 days initial cutting to develop roots.
Temperature to develop roots (range): 20-21° Centigrade.
Crop time (range): 3-5 months to produce a 1-liter container from a rooted cutting.
Habit: Compact.
Suggested container size: 1-liter.
Commercial classification: Flowering perennial.
Use: For container, garden, and landscape.
Type: Ornamental.
Height in 1-liter container (range): 35-40 cm.
Width in 1-liter container: 25 cm.
Cultural requirements: Grow in full sun and moist well-draining soil, with moderate water.
Disease susceptibility: None known to the inventor.
Pest susceptibility: Western flower thrip.
Hardiness: USDA Zone 5.
Special considerations: Generally performs well in poor soils, and under hot dry conditions.

Stem:
- *Branching habit.*—Basal.
- *Stem color.*—183A.
- *Stem length* (*range*).—12-13 cm.
- *Stem width* (*average*).—0.25 cm.
- *Stem shape.*—Cylindrical.
- *Stem surface.*—Villous.
- *Internode* (*range*).—1-2 cm.

Foliage:
- *Type.*—Evergreen.
- *Leaf arrangement* (*range*).—Radical to alternate.
- *Leaf division.*—Simple.
- *Margin.*—Serrate.
- *Leaf shape.*—Oblanceolate.
- *Leaf length* (*average*).—7 cm.
- *Leaf width* (*average*).—1.25 cm.
- *Leaf apex.*—Acute.
- *Leaf base.*—Attenuate.
- *Leaf venation pattern.*—Pinnate.
- *Vein color* (*abaxial surface*).—144D.
- *Vein color* (*adaxial surface*).—144D.
- *Leaf surface* (*abaxial*).—Puberulent.
- *Leaf surface* (*adaxial*).—Pubescent.
- *Leaf attachment* (*range*).—Clasping to petiolate.
- *Petiole dimensions* (*average*).—4 mm. in length and 2 mm. in width.
- *Petiole surface.*—Pubescent.
- *Petiole color.*—Ranges between 144D and 146C.
- *Stipules or spines.*—None observed.
- *Leaf color* (*abaxial surface*).—146B.
- *Leaf color* (*adaxial surface*).—146C.
- *Fragrance.*—None observed.

Inflorescence:
- *Inflorescence type.*—Capitula radiate.
- *Inflorescence quantity* (*average*).—100 per 7-gallon container plant.
- *Aspect.*—Facing upward and outward.
- *Dimensions of inflorescence.*—6 cm. in diameter and 3 cm. in depth.
- *Inflorescence shape.*—Disc.
- *Blooming seasons.*—Summer.
- *Peduncle dimensions* (*average*).—19 cm. in length and 0.25 cm. in diameter.
- *Peduncle shape.*—Cylindrical.
- *Peduncle surface.*—Pubescent.
- *Peduncle color.*—177A.
- *Peduncle strength.*—Strong.
- *Ray flower.*—Bud color: N34A. Bud surface: Pubescent. Bud dimensions: 0.40 cm. in width and 0.60 cm. in length. Bud apex: Rounded. Bud base: Truncate. Bud shape: Ovate. Ray flower shape: Tubular. Ray flower tube dimensions: 15 mm in length; 2 mm in diameter. Ray flower tube color (both surfaces): N34B except basal 2 mm, 2D. Ray flower surface (ventral): Puberulent. Ray flower surface (dorsal): Puberulent. Ray flower arrangement: Radiate. Ray flower quantity (range): 20-25 per inflorescence. Petal quantity (per ray flower): 4 in number. Fused or unfused: Basally fused. Petal margin: Entire. Petal apex: Rounded. Ray flower dimensions: 2.25 cm. in depth and 1.75 cm. in diameter. Petal color (abaxial surface): 46A, 46B and N34B are individually present. Petal color (adaxial surface): 46A, 46B and N34B are individually present. Self-cleaning or persistent: Self-cleaning.
- *Disc floret.*—Shape: Tubular. Surface: Pubescent. Disc floret quantity (per inflorescence): Approximately 125. Disc floret dimensions: 1.50 cm. in depth and <3 mm. in diameter. Disc floret color: 7A (immature florets) all becoming N34A. Disc diameter: 25 mm.
- *Phyllary* (*involucral bracts*).—Phyllary shape: Lanceolate and reflexed. Phyllary color (abaxial surface): 146C and N34A. Phyllary color (adaxial surface): 146C and N34A. Phyllary quantity (average): 30 per inflorescence. Phyllary dimensions (average): 1.50 cm. in length and 0.40 cm. in width. Phyllary surface (abaxial): Villous. Phyllary surface (adaxial): Villous.

Phyllary apex: Cirrhose. Phyllary base: Truncate. Phyllary margin: Entire. Phyllary arrangement: Whorl.

Inflorescence fragrance: Sweet scent observed.

*Lastingness of the inflorescence.*—Ray flowers fall away after 3-5 days.

Reproductive organs:

*Receptacle.*—Shape convex, 10 mm in diameter. 5 mm depth.

*Ray flower.*—Stamen: 4 rudimentary stamens. Stamen color: 161A. Stamen length: 5 mm. Anther: 3 rudimentary anthers. Anther color: 161A. Anther length: <3 mm. Pollen: None observed to date. Pistil: 1 in number. Pistil length: 1.20 cm. Pistil color: 161A and N34A. Stigma: Forked. Stigma color: N34A. Ovary position: Superior. Ovary dimensions: 4 mm. in height and 3 mm. in diameter. Ovary color: 145C. Ovary shape: Ovoid.

*Disc floret.*—Stamen: 4 in number. Stamen length: 5 mm. Stamen color: 162A. Anther: 4 in number. Anther length: 1 mm. Anther color: N186A. Pollen quantity: Heavy. Pollen color: 13A. Pistil: 2 in number. Pistil length: 12 mm. Pistil color: 162A. Stigma: 2 in number. Stigma length: 6 mm. Stigma color: N34A. Stigma shape: Plumose. Ovary: None observed.

*Seed.*—None observed to date.

The invention claimed is:

1. A new and distinct cultivar of *Gaillardia* plant named 'EL FUEGO' as described and illustrated herein.

* * * * *